(12) United States Patent
Liu et al.

(10) Patent No.: US 9,024,035 B2
(45) Date of Patent: May 5, 2015

(54) RADIOTRACER PRECURSOR BANI FOR IMAGING OF HYPOXIC TISSUE, RADIOTRACER, AND METHOD FOR PREPARING THE SAME

(71) Applicant: Atomic Energy Council—Institute of Nuclear Energy Research, Taoyuan County (TW)

(72) Inventors: Show-Wen Liu, Taoyuan County (TW); Yu Chang, Taoyuan County (TW); Cheng-Fang Hsu, Taoyuan County (TW); Sheng-Lun Lin, Taoyuan County (TW); Tsung-Hsien Chiang, Taoyuan County (TW); Chih-Yuan Lin, Taoyuan County (TW)

(73) Assignee: Atomic Energy Council—Institute of Nuclear Energy Research, Taoyuan County (TW)

( * ) Notice: Subject to any disclaimer, the term of this patent is extended or adjusted under 35 U.S.C. 154(b) by 15 days.

(21) Appl. No.: 13/947,222

(22) Filed: Jul. 22, 2013

(65) Prior Publication Data

US 2015/0025248 A1   Jan. 22, 2015

(51) Int. Cl.
*C07F 13/00* (2006.01)
*C07D 233/91* (2006.01)

(52) U.S. Cl.
CPC ............ *C07F 13/005* (2013.01); *C07D 233/91* (2013.01)

(58) Field of Classification Search
CPC ........................... C07F 13/005; C07D 233/91
See application file for complete search history.

(56) References Cited

PUBLICATIONS

Cook et al. "Technetium-99m-labeled HL91 to identify tumor hypoxia: correlation with fluorine-18-FDG." J. Nucl. Med., 1998, vol. 39, pp. 99-103.*

* cited by examiner

*Primary Examiner* — Joseph Kosack
(74) *Attorney, Agent, or Firm* — Rosenberg, Klein & Lee

(57) ABSTRACT

The present invention relates to a radiotracer precursor for imaging of hypoxic tissues, a radiotracer and a method for preparing the same. The radiotracer precursor, BANI, includes a nitroimidazole functional group with a feature of retention in hypoxic tissues and a bifunctional ligand able to complex with radioisotopes. Thus BANI can be used to produce radiotracers retained in hypoxic tissues and the radiotracers are applied to medical imaging of malignant tumor with hypoxic layer.

11 Claims, 4 Drawing Sheets

BANI

RADIOTRACER PRECURSOR BANI FOR IMAGING OF HYPOXIC TISSUE, RADIOTRACER, AND METHOD FOR PREPARING THE SAME

BACKGROUND OF THE INVENTION

1. Fields of the Invention

The present invention relates to a radiotracer precursor, especially to a radiotracer precursor containing an organic ligand, 6-(2-nitroimidazole)hexyl-DL-2,3-Bis-[((triphenylmethyl)thio)acetamido]propanamide (BANI), a radiotracer and a method for preparing the same.

2. Descriptions of Related Art

A plurality of diseases may cause hypoxia and further brings tissues or organs have insufficient oxygen supply. For example, tissues of patients with serious diseases such as stoke, myocardial infarction, malignant tumor, etc. have decreased oxygen supply, hypoxia. The hypoxia is resulted from acute or temporarily reduction of regional blood flow at myocardial cells or insufficient oxygen supply to malignant cells and is unpredictable. Thus a lot of non-invasive techniques for detecting hypoxia at various regions such as heart, brain, tumor have been developed vigorously.

All mammals require oxygen for tissue metabolism. Generally metabolism/reaction in cells only needs low concentration oxygen (about 3~5 torr) flowing from capillaries to cells nearby. But malignant cells change oxygen balance in tissues. Tumor cells need additional oxygen supply to maintain cell activity. In order to meet such requirement, tumor cells induce blood vessel growth in tissues. However, the amount of oxygen the tumor cells require is always much larger than the amount of oxygen the blood vessels supply. Once oxygen diffuses across the wall of capillaries, it is quickly metabolized by cells on outer layers and unable to diffuse into inner layers of tumor cells. Thus cells inside large solid tumors are in hypoxia due to insufficient oxygen and blood supply and necrosis occurs gradually during long term hypoxia. There is a certain ratio of hypoxic or necrosis cells in tumors and the ratio is related to volume and biological characters of tumors.

Therefore hypoxic tissues are of great potential, as media/targets being detected by radionuclide imaging techniques for diagnosis and follow-up of the malignant tumors.

Nuclear medicine imaging involves applications of radioisotopes in medical imaging for patients. Radiopharmaceuticals are delivered into patients' bodies by intravenous injection, oral intake, inhalation etc. After a period of time, the radiopharmaceuticals are attracted to specific organs or tissues. Then medical imaging machines such as gamma cameras are used to detect distribution of the radiopharmaceuticals in organs or tissues. For example, crystal of sodium iodide in the camera scintillates in response to incident gamma radiation so as to form images. After development or computer processing, the images are used by doctors to detect physiological changes.

The drugs available now such as PnAO-NI and HL91 all contain diamine-dioxime ligands that bind to radioisotopes such as $^{99m}Tc$ etc. and apply to radiotracers for imaging hypoxic tissues. Yet $^{99m}Tc$-PnAO-NI has high lipid solubility and $^{99m}Tc$-HL91 has low high lipid solubility. Thus both are not suitable to be used in clinical imaging A suitable radiotracer plays an important role in detection of tumor hypoxia in vivo by radionuclide imaging techniques.

SUMMARY OF THE INVENTION

Therefore it is a primary object of the present invention to provide a radiotracer precursor that includes a nitroimidazole group with a feature of retention in hypoxic tissues and a bifunctional ligand able to complex with radioisotopes. Thus the radioisotopes can be carried to the hypoxic tissues and having a potential used for labeling.

It is another object of the present invention to provide a radiotracer precursor that uses a triphenylmethyl group for protecting thiols. Thus the precursor not only has stable chemical properties but also convenience in storage. The triphenylmethyl group can be released directly during complex reaction before use and this is quite convenient for users.

It is a further object of the present invention to provide a method for effectively preparing a radiotracer precursor with good preservation, convenience, and specificity to hypoxic tissues for labeling.

It is a further object of the present invention to provide a radiotracer that includes both organic functional group with a feature of retention in hypoxic tissues and stable detectable radioisotopes. Morphology of hypoxic tissues, especially the hypoxic layer of malignant tumor can be studied through distribution of radiotracers being detected by associated medical equipment. Thus valuable and sufficient information is provided to doctors for diagnosis.

In order to achieve the above objects, the present invention provides a radiotracer precursor for imaging of hypoxic tissues, a radiotracer and a method for preparing the same. A bifunctional ligand is attached with a nitroimidazole or a nitroimidazole derivative and then coupled to a radioisotope for labeling by complex reaction so as to form a radiotracer for hypoxic tissues. The radiotracer for hypoxic tissues is not only used for diagnosis but also applied to follow-up after treatment. Thus the radiotracer for hypoxic tissues plays an essential role in diagnosis and treatment of malignant tumors.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Please refer to following embodiments for details, features and effects of the present invention.

Figure 1:
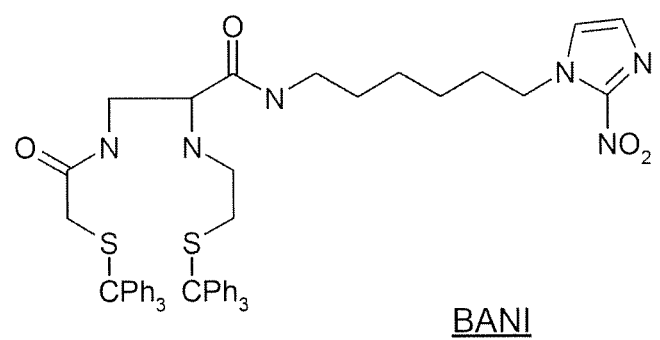
FIG. 1 shows a chemical structure of an embodiment of a radiotracer precursor according to the present invention.

Refer to FIG. 1, a schematic drawing showing a chemical structure of a radiotracer precursor of the present invention is revealed. As shown in figure, BANI mentioned above includes a long alkyl group and a nitroimidazole so as to increase its lipid solubility. Moreover, nitroimidazole or its derivatives will have a series of redox-reactions after entering cells.

Moreover, after entering hypoxic cells, nitroimidazole is gradually reduced to amine by Xanthine oxidase. Due to the increased molecular polarity, the reduced amine is unable to pass cell membrane and is retained inside the cell. On the other hand, in the cell having normal oxygen, the amine is oxidized to nitro by oxygen and is able to leave the cell.

In other words, if now the cell contains sufficient oxygen, nitroimidazole or its derivatives are exported out of the cell to be excreted quickly. If the cell is in hypoxia, nitroimidazole or its derivatives are going to retain for a longer period. Due to retention of nitroimidazole in hypoxia tissue, nitroimidazole is labeled with radioisotopes to form hypoxia imaging agents with excellent performance.

The radiotracer precursor not only includes nitroimidazole but also a bifunctional ligand that binds to radioactive isotopes in a five-coordinated manner to form a substance with stable pyramid structure. The substance can be used as a radiotracer.

The radiotracer precursor of the present invention includes nitroimidazole with a feature of retention in hypoxic tissues as mentioned above. In malignant tumor, cancer cells grow rapidly so that most of tumor has a feature of hypoxia. After being labeled with radioisotopes, the radiotracer produced can retain in malignant tumor, used as the imaging tracer.

Moreover, the thiol group of BANI is protected so that the chemical properties are stable and the storage time is extended. Thiols are easily oxidized in neutral or alkaline solution. The oxidized thiol group is unable to react with radioisotopes. Thus the thiols need to be protected first. There are several ways to protect the thiol group such as the use of 4-methoxybenzyl or triphenylmethyl ($CPh_3$). The bond energy between triphenylmethyl group and sulfur atom is lower. When heavy metals are present, the bond therebetween is easy to break and a bond between heavy metals and sulfur atom is formed. Thus the use of triphenylmethyl group as a thiol-protecting group is preferred and the reaction conditions are simple. Only boron trifluoride ethyl ether complex is added and thiol is converted to triphenylmethylthio for protection.

Figure 2:
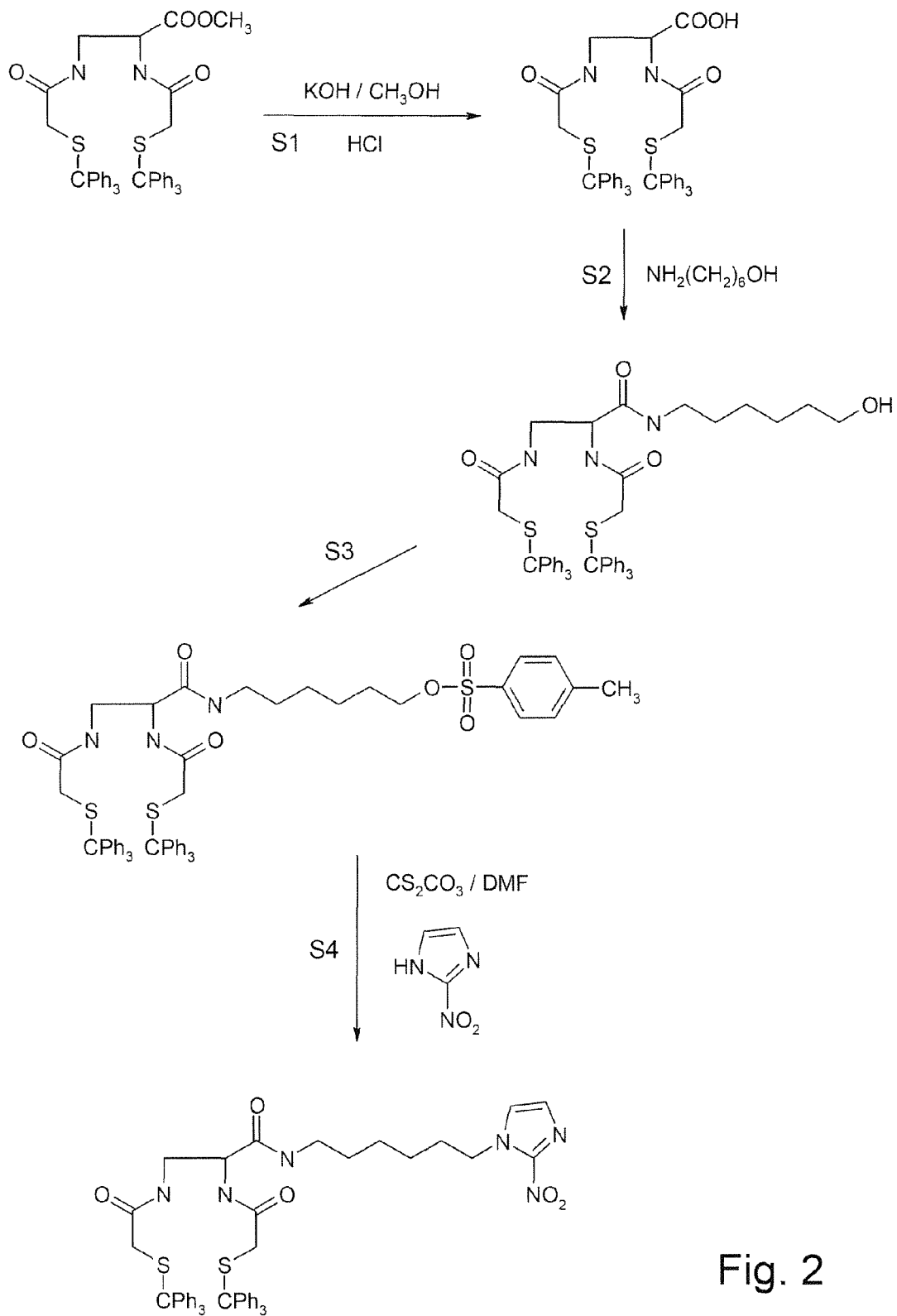
FIG. 2 is a schematic diagram showing the synthesis of BANI according to the present invention.

Refer to FIG. 2, a method for preparing a radiotracer precursor of the present invention is disclosed. The method includes following steps:

STEP S1: hydrolyze methyl-DL-2,3-bis[((triphenylmethyl)-thio)acetamido]propionate to get DL-2,3-Bis-[((triphenylmethyl)thio)acetamido]propionic acid;

STEP S2: take 6-aminohexanol and DL-2,3-Bis-[((triphenylmethyl)thio)acetamido]propionic acid to carry out amidation and get 6-hydroxyhexyl DL-2,3-Bis[((triphenylmethyl)thio)acetamido]-propanamide;

STEP S3: use P-toluenesulfornyl chloride and 6-hydroxyhexyl DL-2,3-Bis[((triphenylmethyl)thio)acetamido]propan-amide to perform a substitution reaction and produce 6-toluenesulfonylhexyl-DL-2,3-Bis-[((triphenylmethyl)-thio)acetamido]propanamide;

STEP S4: take 2-nitroimidazole and 6-toluenesulfonylhexyl-DL-2,3-Bis[((triphenylmethyl)-thio)acetamido]propanamide to carry out substitution reaction and get BANI.

The hydrolysis reaction in the steps S1 uses potassium hydroxide (KOH) or sodium methoxide ($CH_3NaO$) as a catalyst, being carried out in methanol solution ($CH_3OH$). Hydrochloric acid is used for neutralization.

In the step S2, before carrying out the amidation, the carboxyl acid of DL-2,3-Bis-[((triphenylmethyl)thio)-acetamido]propionic acid is activated first. Then use 1,3-dicyclohexylcarbodiimide (DCC) and N-hydroxysuccinimide (NHS) as reactants to react in trichloromethane solution (chloroform, $ChCl_3$) for amidation. The reaction temperature is 50 degrees Celsius and the reaction time is 24 hours.

The substitution reaction in the step S3 is performed in pyridine solution and the solvent is dichloromethane ($CH_2Cl_2$). The reaction temperature is room temperature and the reaction time is 3 hours.

The substitution reaction in the step S4 is reacted in anhydrous dimethylformamide (DMF) solution and Caesium carbonate ($Cs_2CO_3$) is used as a reactant. The reaction temperature is 70 degrees Celsius and the reaction time is 24 hours.

Figure 3:
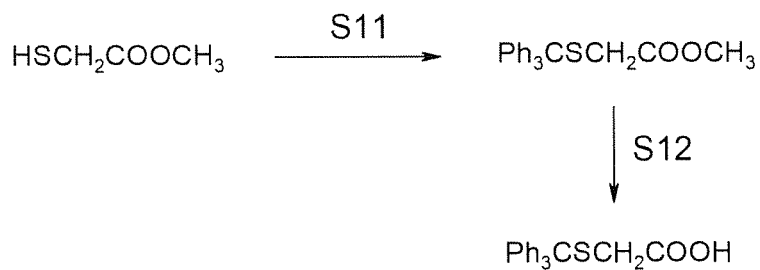
FIG. 3 is a schematic diagram showing the synthesis of a compound used for preparing BANI according to the present invention.
Figure 4:
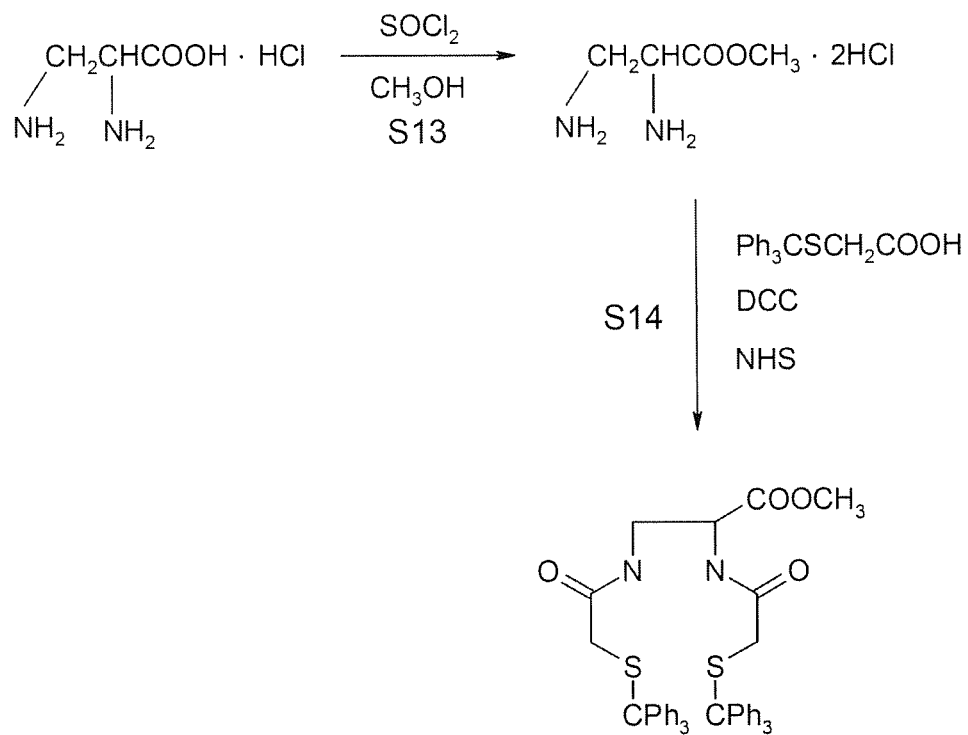
FIG. 4 is a schematic diagram showing the synthesis of a compound used for preparing BANI according to the present invention.

Refer to FIG. 3 and FIG. 4, a method for preparing DL-2,3-bis[((tri phenylmethyl)-thio) acetamido]-propionate used in the step S1 includes following steps:

Step S11: use a triphenylmethyl group to protect a thiol group of thioglycolic acid methyl ester and get triphenylmethyl thioglycolic acid methyl ester;

Step S12: hydrolyze triphenylmethyl thioglycolic acid methyl ester to produce triphenylmethyl thioglycolic acid;

Step S13: perform esterification of DL-2,3-diaminopropionic acid in methanol to get methyl DL-2,3-diamino-propionate; and Step S14: use methyl DL-2,3-diamino-propionate and triphenylmethyl thioglycolic acid to perform amidation and get DL-2,3-bis[((triphenylmethyl)-thio)acetamido]propionate.

In the step S11, the catalyst is boron trifluoride ethyl ether complex while protecting thiol group by triphenylmethyl group. The solvent is trichloromethane (chloroform). The reaction temperature is room temperature and the reaction time is 5 hours.

In order to remove thiol protecting groups, BANI is dissolved in trifluoroacetic acid and add overdose triethylsilane into the solution. Thus triphenylmethyl group is released from thiol group to form solid that is insoluble in trifluoroacetic acid. Then the solid can be removed by filtration or wash with n-hexane. These methods are simple and convenient.

The hydrolysis reaction in the step S12, similar to that in the step S1, potassium hydroxide or sodium methoxide is used as a catalyst, being carried out in methanol solution.

In the amidation of the step S14, DCC and NHS are used as reactants to react in anhydrous tetrahydrofuran (THF) solution at room temperature for 1 hour. Moreover, the mole number of DL-2,3-diamino-propionate in the amidation reaction is two times than that of triphenylmethyl thioglycolic acid.

According to the above steps, organic ligand BANI is prepared. The 2-nitroimidazole of BANI retains in hypoxic tissues such as the hypoxic layer of malignant tumor generated due to rapid growth of tumor cells. Thus BANI has more advantages while being used as a radiotracer. The bifunctional ligand contained in BANI can also complex with radioisotopes so as to be detected by associated medical equipment.

Figure 5:
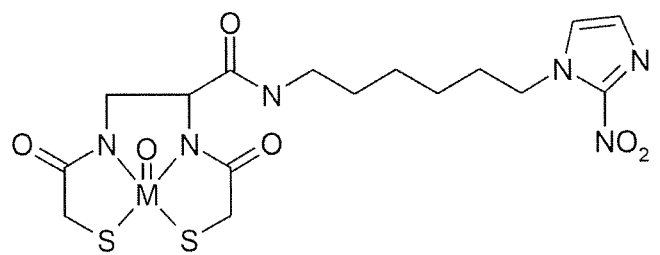
FIG. 5 shows a chemical structure of an embodiment of a radiotracer according to the present invention.

Refer to FIG. 5, a radiotracer containing the BANI organic ligand for imaging of hypoxia tissues is revealed. The difference between the radiotracer and the radiotracer precursor is in that BANI in the radiotracer has already connected with a radioisotope M. The triphenylmethyl group for protection is automatically released during complex reaction and there is no need to remove the protection group in advance. M is selected from one of the most common radioisotopes used in radionuclide imaging such as technetium-99m ($^{99m}Tc$) or Rhenium-188 ($^{188}Re$). In this embodiment, $^{99m}Tc$ is preferred. The half life of $^{99m}Tc$ is 6 hours and such period is proper. Its gamma energy is 140.6 KeV and absorption by human tissues is low. Moreover, $^{99m}Tc$ is produced in a nuclear reactor and is convenient to use. The cost is low and there is no need to go through the purification process.

After entering living bodies, the radiotracer retains in hypoxic tissues such as malignant tumor due to the 2-nitroimidazole group of the organic ligand BANI. Thus through PET (positron emission tomography) or SPET (single photon emission tomography) that detects distribution of radioisotopes ($^{99m}Tc$, $^{188}Re$, etc.), the malignant tumor can be imaged and observed clearly. Thus an accurate diagnosis is made and healthcare quality is improved dramatically.

The followings are embodiments for preparing BANI.

Synthesis of Triphenylmethyl Thioglycolic Acid Methyl Ester

Dissolve 5.0 mL (55.0 mmol) methyl thioglycolate and 14.3 g (55.0 mmol) triphenylmethanol in 80 mL trichloromethane. Then slowly drop 6.9 mL (55.0 mmol) boron trifluoride ethyl ether complex into the solution and stir the solution at room temperature. Use thin layer chromatography (TLC)(chloroform:hexane=1:1) to follow the reaction. After starting material disappeared completely, wash the reaction solution with water (2×100 mL). The organic phase is dried by anhydrous sodium sulfate and then the solvent is removed by vacuum evaporation to get 18.6 g (97.5%) triphenylmethyl thioglycolic acid methyl ester (hereafter referred to as compound 1).

Synthesis of Triphenylmethyl Thioglycolic Acid

Take and dissolve 18.6 g (53.5 mmol) compound 1 in 300 mL 10% potassium hydroxide in methanol solution and stir the solution at room temperature until the compound 1 being dissolved completely. After being concentrated by vacuum concentration, dissolve residue with 100 mL 50% methanol aqueous solution and drop concentrated hydrochloric acid into the solution until the pH value of the solution is 6. Use trichloromethane solution to extract (3×100 mL). Then after the organic phase being dried by anhydrous sodium sulfate and the solvent being removed by vacuum evaporation, 17.9 g, (~400%) triphenylmethyl thioglycolic acid is obtained (hereafter referred to as compound 2).

Synthesis of Methyl DL-2,3-diaminopropionate Dihydrochloride

Dissolve 5.0 g (35.6 mmol) DL-2,3-diaminopropionic acid monohydrochloride in 500 mL methanol. Being cooled down in an ice bath, slowly drop 25 mL thionyl chloride into the solution. Then remove the ice bath and stir the mixture at room temperature overnight. Next the mixture is concentrated by vacuum concentration to get 6.8 g (100%) colorless solid DL-2,3-diaminopropionic acid monohydrochloride (hereafter referred to as compound 3)

Synthesis of Methyl DL-2,3-bis[((triphenylmethyl)thio)-acetamido]propionate (1) Dissolve 0.57 g (3.0 mmol) compound 3 in 20 mL methanol and then add 10 mL methanol solution with 0.33 g 6.0 mmol potassium hydroxide. After the solution being stirred for 5 minutes, filter the solution and remove the solvent by vacuum evaporation.
(2) Dissolve 2.0 g (6.0 mmol) compound 2, 1.85 g (9.0 mmol) 1,3-dicyclohexyl-carbodiimide and 0.83 g (7.2 mmol) N-hydroxysuccinimide in 60 mL anhydrous Tetrahydrofuran (THF) solution. Stir the solution for 1 hour and a solid precipitates. Remove the solid after vacuum filtration.
(3) Pour the filtrate obtained in the step (2) into the residue obtained in the step (1) and the stir the mixture overnight. After filtration, dry the filtrate by vacuum evaporation. Extract residue by dichloromethane (2×30 mL). Wash the combined dichloromethane solution with water, add with anhydrous sodium sulfate for dehydration, and concentrate the solution by vacuum concentration. Use liquid chromatography ($SiO_2$, $CHCl_3$:EtOAc=4:1) to get 1.3 g (57%) solid product (hereafter referred to as compound 4).

Synthesis of DL-2,3-Bis[(((triphenylmethyl)thio)-acetamido]propionic Acid

Dissolve 0.7 g (0.9 mmol) compound 4 in 10 mL 10% potassium hydroxide in methanol solution, stir the solution for 30 minutes and cool down the solution in an ice bath. Then add 20 mL water and 6N hydrochloric acid for adjusting the pH value of the solution to 6.0. Use trichloromethane solution to extract (3×80 mL). Remove water in combined extracted trichloromethane solution by anhydrous sodium sulfate and then remove the solvent by vacuum evaporation so as to get 0.7 g (100%) product (hereafter referred to as compound 5).

Synthesis of 6-hydroxyhexyl DL-2,3-Bis[(((triphenylmethyl)thio)acetamido]propanamide Add 1.06 g (1.44 mmol) compound 5, 0.20 g (1.73 mmol) N-hydroxysuccinimide, 0.45 g (2.16 mmol) 1,3-dicyclohexylcarbodiimide, and 0.17 g (1.44 mmol) 6-aminohexanol into 100 mL chloroform, heat the solution to 50° C. and stir the solution overnight. After being treated by vacuum concentration, add acetone for dissolution. Then perform vacuum filtration, get the filtrate and concentrate the filtrate. Use liquid chromatography ($SiO_2$, $CHCl_3$:$CH_3OH$=95:5) for isolation and purification of the product (0.54 g, 45%)(hereafter referred to as compound 6).

Synthesis of 6-toluenesulfonylhexyl DL-2,3-Bis-[(((triphenylmethyl)thio)acetamido]propanamide Dissolve 0.55 g (0.66 mmol) compound 6 in 10 mL anhydrous dichloromethane and 1 mL anhydrous pyride. Then slowly add 0.50 g (2.63 mmol) P-toluenesulfonyl chloride into the solution in an ice bath and stir the mixture at room temperature for 3 hour. Next add 10 mL water and concentrated hydrochloric acid for adjusting the pH value of the mixture to less than 7. Use 80 mL dichloromethane to extract twice. Take the organic layer, wash with 1N hydrochloric acid aqueous solution. Take the organic layer, add with anhydrous sodium sulfate for dehydration, and remove the solvent by vacuum evaporation. Use liquid chromatography ($SiO_2$, $CHCl_3$:$CH_3OH$=95:5) for isolation and purification to get the product 0.42 g (65%) (hereafter referred to as compound 7).

Synthesis of 6-(2-nitroimidazole)hexyl-DL-2,3-Bis-[(((triphenylmethyl)thio)acetamido]propanamide, BANI Take 0.44 g (0.45 mmol) compound 7, 0.05 g (0.45 mmol) 2-nitroimidazole, and 0.15 g (0.45 mmol) $Cs_2CO_3$, add with 10 mL anhydrous DMF. Heat the mixture to 70° C. and stir the mixture overnight. Then vacuum heat to 50° C. for evaporation and add chloroform for dissolution. Take the dissolved part and concentrate the dissolved part by vacuum concentration. Use liquid chromatography ($SiO_2$, $CHCl_3$:$CH_3OH$=95:5) for isolation and purification of the product 0.18 g (42%) BANI.

The BANI prepared according to the above steps is with good preservation. Before use, the BANI complexes with a radioisotope to form a radiotracer that is able to retain in hypoxic tissues through the effect of the functional group of BANI. At the same time, BANI makes the radioisotope precisely reach the hypoxic tissues inside living bodies to be used as an imaging tracer. Thus the radiotracer precursor for hypoxic tissues, the radiotracer and the method for preparing the same according to the present invention are of high practical value.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A radiotracer precursor as represented by the following structural formula:

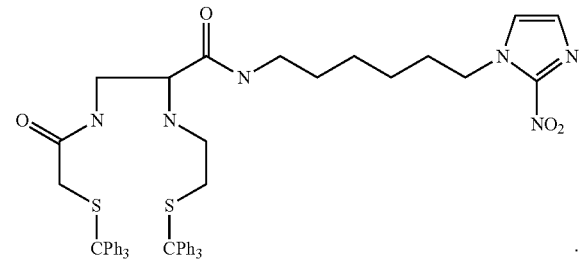

2. A method for preparing a radiotracer precursor comprising the steps of:
   hydrolyzing methyl-DL-2,3-bis[(((triphenylmethyl)-thio)acetamido]propionate to get DL-2,3-Bis-[(((triphenylmethyl)thio)acetamido]propionic acid;
   using 1,3-dicyclohexylcarbodiimide (DCC) and N-hydroxysuccinimide (NHS) as reactants to react in trichloromethane solution (chloroform, ChCl3) for amidation;
   using 6-aminohexanol and DL-2,3-Bis-[(((triphenyl-methyl)thio)acetamido]propionic acid to carry out amidation and get 6-hydroxyhexyl DL-2,3-Bis[(((triphenylmethyl)thio)acetamido]propanamide;
   using P-toluenesulformyl chloride and 6-hydroxyhexy-lDL-2,3-Bis[(((triphenylmethyl)thio)acetamido]-propanamide to perform a substitution reaction and produce 6-toluenesulfonylhexyl-DL-2,3-Bis-[(((triphenylmethyl)-thio)acetamido]propanamide; and
   taking 2-nitroimidazole and 6-toluenesulfonylhexyl-DL-2,3-Bis[(((triphenyl-methyl)-thio)acetamido]propanamide to carry out substitution reaction and get 6-(2-nitroimidazole)hexyl-DL-2,3-Bis-[(((triphenylmethyl)thio)acetamido]propanamide.

3. The method as claimed in claim 2, wherein a method for preparing DL-2,3-bis[(((triphenylmethyl)-thio)-acetamido] propionate includes the steps of:
   using a triphenylmethyl group to protect a thiol group of thioglycolic acid methyl ester and get triphenylmethyl thioglycolic acid methyl ester;
   hydrolyzing triphenylmethyl thioglycolic acid methyl ester to produce triphenylmethyl thioglycolic acid;
   performing esterification of DL-2,3-diaminopropionic acid in methanol to get methyl DL-2,3-diamino-propionate; and
   using methyl DL-2,3-diamino-propionate and triphenylmethyl thioglycolic acid to perform amidation and get DL-2,3-bis[(((triphenylmethyl)-thio)acetamido]propionate.

4. The method as claimed in claim 2, wherein in the step of hydrolyzing, potassium hydroxide or sodium methoxide is used as a catalyst and the reaction occurs in methanol solution.

5. The method as claimed in claim 3, wherein in the step of hydrolyzing, potassium hydroxide or sodium methoxide is used as a catalyst and the reaction occurs in methanol solution.

6. The method as claimed in claim 3, wherein in the step of using a triphenylmethyl group to protect a thiol group, boron trifluoride ethyl ether complex is used as a catalyst and the solvent is trichloromethane; reaction temperature is room temperature and reaction time is 5 hours.

7. The method as claimed in claim 2, wherein in the step of using 1,3-dicyclohexylcarbodiimide (DCC) and N-hydroxysuccinimide (NHS) as reactants to react in trichloromethane solution (chloroform, ChCl3), reaction temperature of 1,3-dicyclohexylcarbodiimide (DCC) and N-hydroxysuccinimide (NHS) is 50 degrees Celsius and reaction time is 24 hours.

8. The method as claimed in claim 3, wherein in the step of using methyl DL-2,3-diamino-propionate and triphenylmethyl thioglycolic acid to perform amidation, 1,3-dicyclohexylcarbodiimide (DCC) and N-hydroxysuccinimide (NHS) are used as reactants to react in anhydrous tetrahydrofuran (THF) solution at room temperature for 1 hour.

9. The method as claimed in claim 2, wherein in the step of using P-toluenesulformyl chloride and 6-hydroxyhexyl DL-2,3-Bis[(((triphenylmethyl)thio)acetamido]-propanamide to perform a substitution reaction, the substitution reaction occurs in pyridine solution and a solvent used is dichloromethane (CH2Cl2); reaction temperature is room temperature and reaction time is 3 hours.

10. The method as claimed in claim 2, wherein in the step of taking 2-nitroimidazole and 6-toluenesulfonylhexyl-DL-2,3-Bis[(((triphenyl-methyl)-thio)acetamido]-propanamide to carry out substitution reaction, the substitution reaction is reacted in anhydrous dimethylformamide (DMF) solution and Caesium carbonate ($Cs_2CO_3$) is used as a reactant; reaction temperature is 70 degrees Celsius and reaction time is 24 hours.

11. A radiotracer as represented by the following structural formula:

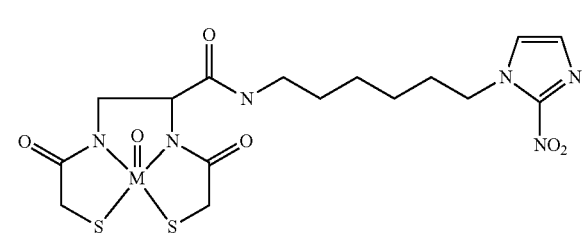

wherein M is selected from the group consisting of technetium-99m and Rhenium-188.

* * * * *